United States Patent
Shanley et al.

(10) Patent No.: US 7,429,268 B2
(45) Date of Patent: Sep. 30, 2008

(54) EXPANDABLE MEDICAL DEVICE WITH DIFFERENTIAL HINGE PERFORMANCE

(75) Inventors: John F. Shanley, Redwood City, CA (US); Beau M. Fisher, Danville, CA (US)

(73) Assignee: Innovational Holdings, LLC, New Brunswick, NJ (US)

( * ) Notice: Subject to any disclaimer, the term of this patent is extended or adjusted under 35 U.S.C. 154(b) by 64 days.

(21) Appl. No.: 11/266,092

(22) Filed: Nov. 2, 2005

(65) Prior Publication Data

US 2006/0122688 A1 Jun. 8, 2006

Related U.S. Application Data

(60) Provisional application No. 60/634,335, filed on Dec. 8, 2004.

(51) Int. Cl.
*A61F 2/06* (2006.01)
(52) U.S. Cl. .................................................... 623/1.15
(58) Field of Classification Search ........ 623/1.11–1.35
See application file for complete search history.

(56) References Cited

U.S. PATENT DOCUMENTS

| | | | |
|---|---|---|---|
| 5,064,435 A | 11/1991 | Porter | |
| 5,716,393 A | 2/1998 | Lindenberg et al. | |
| 5,843,117 A | 12/1998 | Alt et al. | |
| 5,922,020 A * | 7/1999 | Klein et al. | 623/1.15 |
| 6,027,526 A | 2/2000 | Limon et al. | |
| 6,210,429 B1 | 4/2001 | Vardi et al. | |
| 6,245,101 B1 * | 6/2001 | Drasler et al. | 623/1.15 |
| 6,273,910 B1 | 8/2001 | Limon | |
| 6,273,911 B1 | 8/2001 | Cox et al. | |
| 6,290,673 B1 | 9/2001 | Shanley | |
| 6,468,302 B2 | 10/2002 | Cox et al. | |
| 6,511,505 B2 | 1/2003 | Cox et al. | |
| 6,540,774 B1 | 4/2003 | Cox | |
| 6,602,281 B1 * | 8/2003 | Klein | 623/1.15 |
| 6,602,284 B2 | 8/2003 | Cox et al. | |
| 6,706,061 B1 | 3/2004 | Fischell et al. | |
| 6,706,062 B2 | 3/2004 | Vardi et al. | |
| 6,796,997 B1 | 9/2004 | Penn et al. | |
| 6,835,203 B1 * | 12/2004 | Vardi et al. | 623/1.34 |
| 6,852,124 B2 | 2/2005 | Cox et al. | |
| 6,855,125 B2 | 2/2005 | Shanley | |
| 6,896,696 B2 | 5/2005 | Doran et al. | |
| 6,899,729 B1 | 5/2005 | Cox et al. | |
| 6,945,992 B2 | 9/2005 | Goodson et al. | |
| 6,962,603 B1 | 11/2005 | Brown et al. | |
| 6,981,986 B1 | 1/2006 | Brown et al. | |

(Continued)

FOREIGN PATENT DOCUMENTS

EP 541443 1/1996

(Continued)

*Primary Examiner*—Suzette J Gherbi

(57) ABSTRACT

The stent described herein is configured with expandable rings at either end of the stent having increased radial strength compared to the expandable middle rings. This difference between the configuration of the stent at the middle and ends of the stent results in more even expansion properties of the stent, better crimping properties of the stent, and uniform diameter post deployment. The expandable rings are formed by a plurality of struts and a plurality of ductile hinges arranged such that upon expansion, the ductile hinges are deformed while the struts are not deformed.

12 Claims, 3 Drawing Sheets

U.S. PATENT DOCUMENTS

| | | |
|---|---|---|
| 2001/0027291 A1 | 10/2001 | Shanley |
| 2002/0165604 A1 | 11/2002 | Shanley |
| 2003/0105511 A1 | 6/2003 | Welsh et al. |
| 2004/0106973 A1* | 6/2004 | Johnson .................. 623/1.11 |
| 2005/0059991 A1 | 3/2005 | Shanley |
| 2005/0113903 A1 | 5/2005 | Rosenthal et al. |
| 2005/0203605 A1 | 9/2005 | Dolan |
| 2006/0122688 A1 | 6/2006 | Shanley et al. |
| 2006/0178735 A1 | 8/2006 | Litvack et al. |

FOREIGN PATENT DOCUMENTS

| | | |
|---|---|---|
| EP | 800801 | 10/1997 |
| EP | 821921 | 8/2001 |
| EP | 1493401 | 1/2005 |
| EP | 1512381 | 3/2005 |
| EP | 1470796 | 6/2005 |
| EP | 1189554 | 8/2005 |
| WO | WO-9936002 | 7/1999 |
| WO | WO-05018499 | 3/2005 |
| WO | WO-05092244 | 10/2005 |
| WO | WO-06036319 | 4/2006 |

* cited by examiner

EXPANDABLE MEDICAL DEVICE WITH DIFFERENTIAL HINGE PERFORMANCE

CROSS-REFERENCE TO RELATED APPLICATIONS

This application claims priority to U.S. Provisional Patent Application Ser. No. 60/634,335, filed Dec. 8, 2004, the entire contents of which are incorporated herein by reference.

BACKGROUND OF THE INVENTION

1. Field of the Invention

The invention relates to an expandable medical device, such as a stent, and more particularly, the invention relates to an expandable medical device having hinges or strain concentration features.

2. Description of the Related Art

Permanent and biodegradable stents are used for implantation within a body passageway to maintain patency of the passageway. Coronary stents are typically introduced percutaneously, and transported transluminally until positioned at a desired location. These stents are then expanded either mechanically, such as by the expansion of a balloon positioned inside the device, or expand themselves by releasing stored energy upon actuation within the body. When the stent is permanent and expanded within the lumen, the stent becomes encapsulated within the body tissue and remains a permanent implant. When the stent is biodegradable and expanded within the lumen, the stent becomes encapsulated within the body tissue and degrades over time.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665; 4,739,762; and 4,776,337). Known construction materials for use in stents include polymers, organic fabrics, biocompatible metals, such as stainless steel, gold, silver, tantalum, titanium, and shape memory alloys, such as Nitinol.

Many stents are delivered to an implantation site and deployed by a balloon catheter. Balloon expandable stents are mounted on a balloon at a distal end of a balloon catheter and expanded by inflation of the balloon. However, as the balloon is inflated, often the ends of the balloon and stent will expand first followed by expansion of the center of the balloon and stent. This expansion in a dumbbell shape can result in displacement of the lesion toward the center of the stent.

The stent can also recoil inward after expansion. However, the ends of the stent can recoil further than a center portion due to concentration of the inward forces applied by the vessel walls on the ends of the stent. This can result in an implanted stent with inwardly tapering ends.

Accordingly, it would be desirable to provide an expandable medical device, such as a stent, having improved uniformity during expansion and/or improved uniformity after expansion.

SUMMARY OF THE INVENTION

The present invention relates to an expandable medical device having reduced sections or hinges with differing performance depending on their location on the device.

In accordance with one aspect of the invention, an expandable medical device includes at least one middle expandable ring formed of a plurality of substantially rigid struts interconnected by deformable ductile hinges and two end expandable rings one located at each opposite axial end of the expandable medical device and interconnected to the at least one middle expandable ring by flexible connecting elements. The end expandable rings are formed of a plurality of substantially rigid struts interconnected by deformable ductile hinges. The ductile hinges of the at least one middle expandable ring have a hinge width less than a hinge width of the ductile hinges of the end expandable rings.

In accordance with another aspect of the invention, a method of improving crimping of stents onto balloons comprises the steps of forming a stent with a plurality of struts and a plurality of ductile hinges, forming a portion of the plurality of ductile hinges located at axial ends of the stent with a larger width than a remainder of the plurality of ductile hinges, crimping the stent onto a balloon catheter by compressing the stent to a uniform crimped diameter along the axis of the stent, and releasing the compressive force of crimping and causing the stent to recoil a first percentage at the axial ends of the stent and a second percentage at a middle portion of the stent, wherein the second percentage is greater than the first percentage. The ductile hinges are designed to deform plastically upon radial expansion or compression of the stent while the struts experience substantially no plastic deformation upon radial expansion or compression.

In accordance with a further aspect of the invention, a stent and delivery system includes a balloon catheter and a stent crimped onto the balloon catheter, wherein a crimped center portion of the stent has a first diameter which is greater than second and third diameters of opposite end portions of the stent.

BRIEF DESCRIPTION OF THE DRAWING FIGURES

The invention will now be described in greater detail with reference to the preferred embodiments illustrated in the accompanying drawings, in which like elements bear like reference numerals, and wherein.

DETAILED DESCRIPTION

Figure 1A:
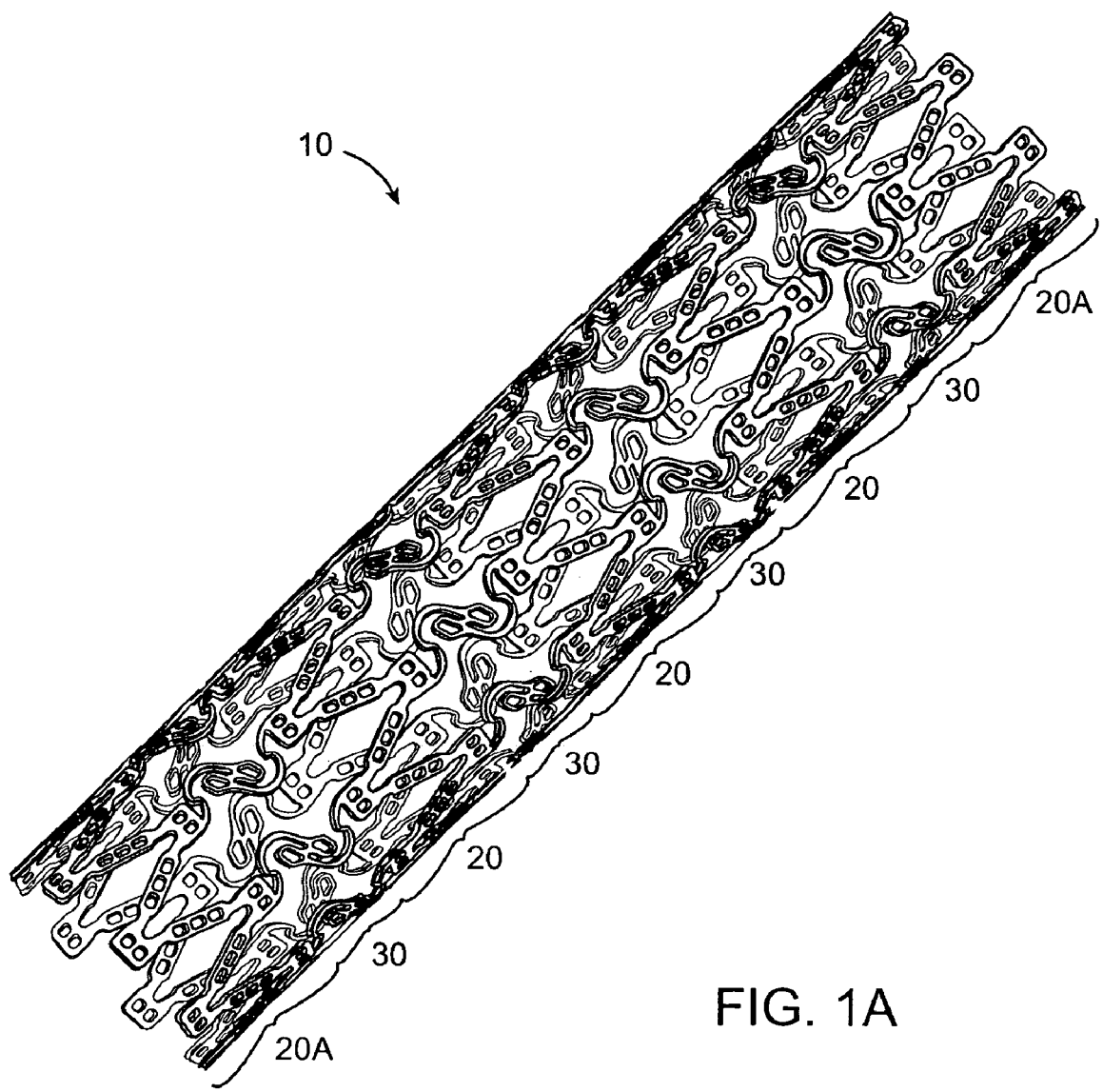
FIG. 1A is an enlarged perspective view of one example of a stent according to the present invention in a semi expanded configuration.
Figure 1B:
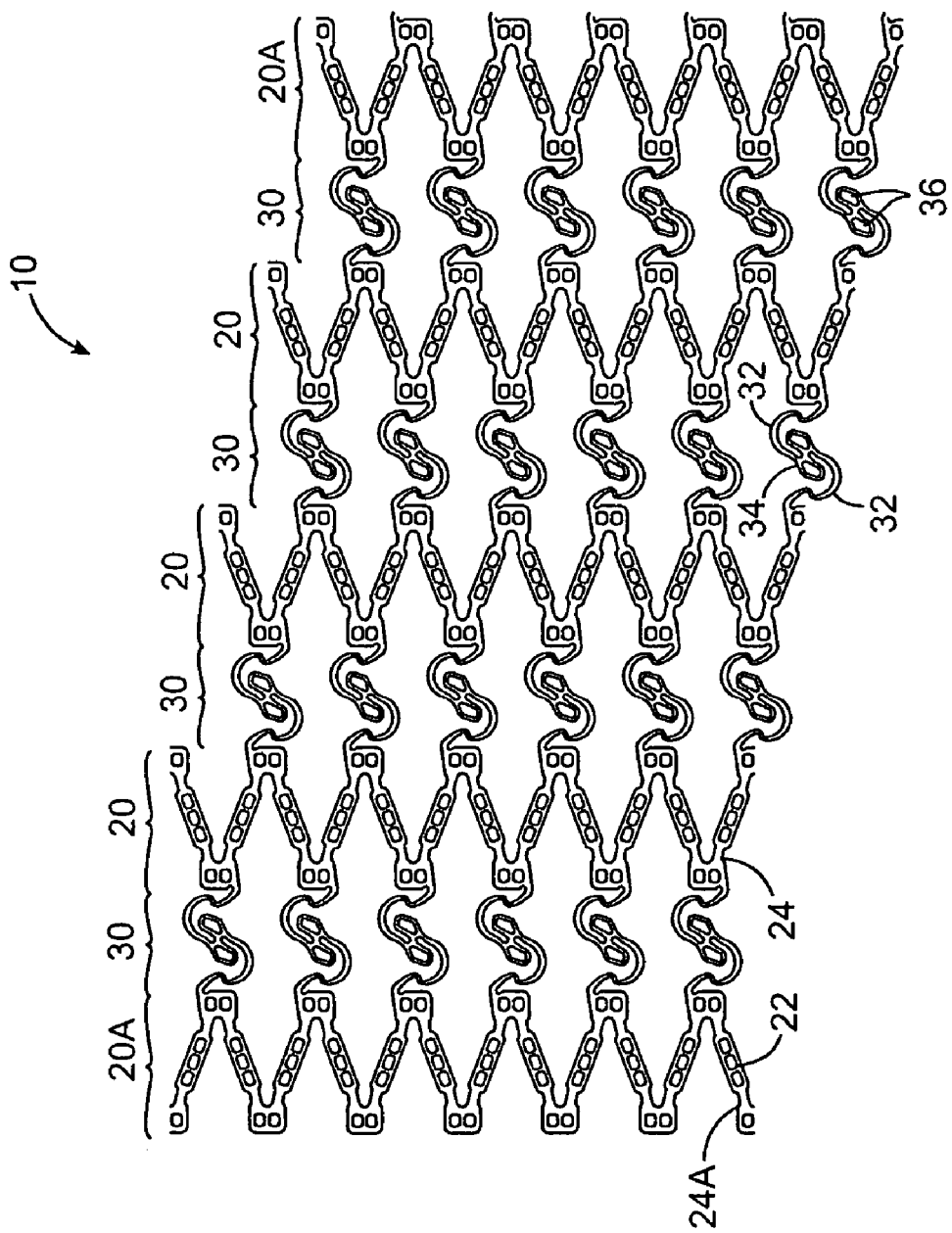
FIG. 1B is a top view of the stent of FIG. 1A which has been unrolled and laid flat.
Figure 2:
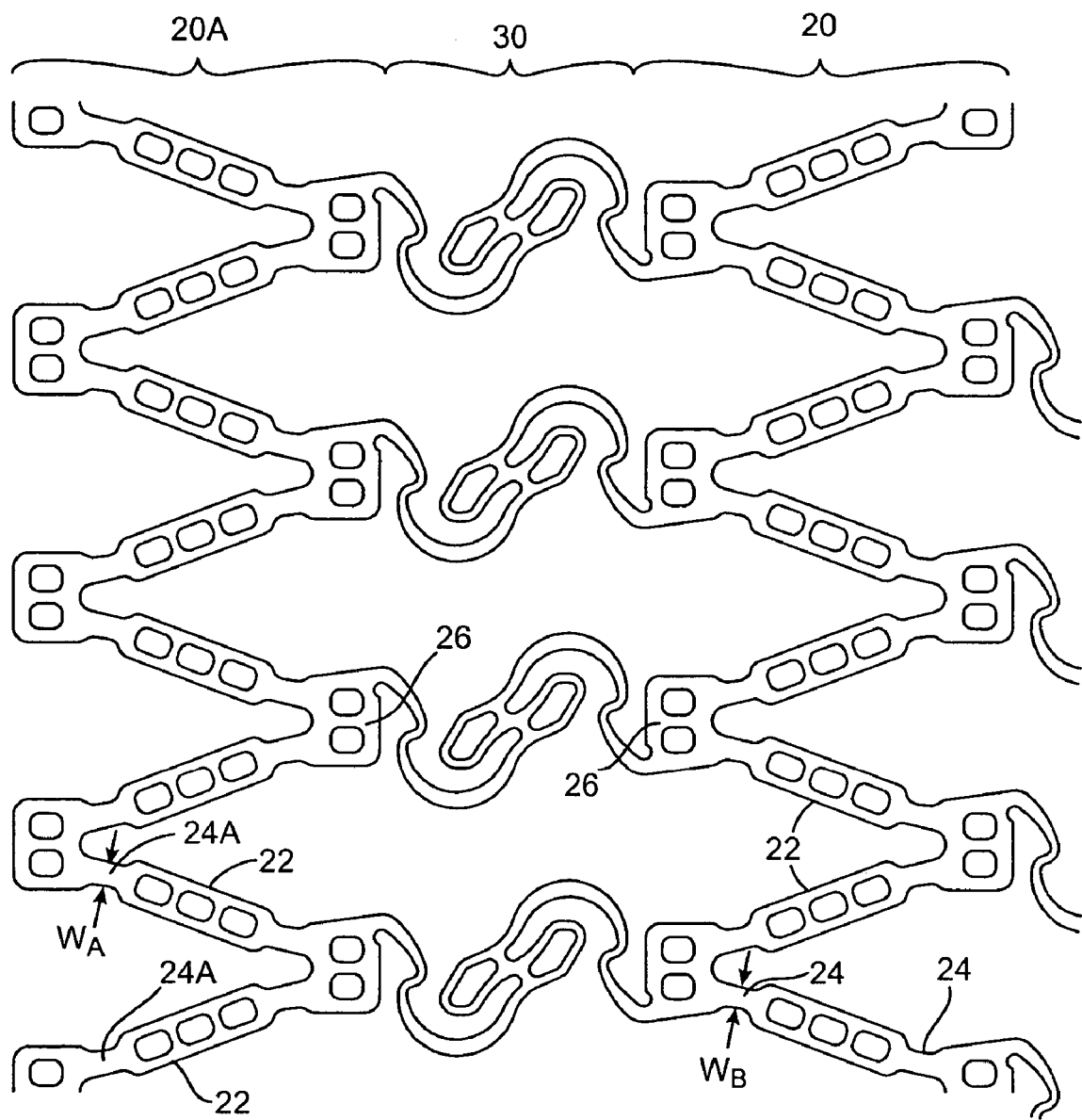
FIG. 2 is an enlarged view of a portion of the stent of FIGS. 1A and 1B.

FIGS. 1A, 1B, and 2 illustrate a stent 10 formed from a plurality of expandable rings 20 and a plurality of flexible bridging elements 30 connecting the rings. The stent 10 is expandable from an insertion configuration to an expanded implanted configuration by deployment of an expanding device, such as a balloon catheter. The stent 10 is illustrated in a partially expanded configuration for ease of illustration. The expandable rings 20 provide radial hoop strength to the stent while the flexible bridging elements 30 allow the stent to flex axially during delivery and after implantation. The stent 10 is configured with expandable rings having different configurations for the end rings 20A and the middle rings 20 to achieve improved crimping, expansion, and post-expansion properties of the stent.

The expansion of a stent by a balloon catheter involves mounting the stent on the balloon and inflating the balloon with a fluid. When the balloon inflates, the first portions of the balloon to inflate are the end portions outside the boundaries of the stent. This is due to the constraining forces of the stent impeding the expansion of the portion of the balloon under the stent. The balloon then inflates inward from the ends creating a slight hourglass shape in the stent and balloon during expansion. Upon complete expansion, the stent will generally reach an even expansion eliminating the hourglass effect due to the relatively fixed shape of the inelastic balloons used to deploy the stents.

When the stent is enlarged in an artery in this hourglass shape, the lesion can be remodeled toward a center of the stent creating a densified lesion and an undesirable narrowing in the center of the stent. In addition, when the stent is deployed at a bifurcation, the hourglass shaped expanding profile of the stent can displace the lesion toward the junction of the bifurcation and possibly increasing occlusion of the branch vessel.

In the event that a stent opens in an hourglass shape with one end opening first, the stent can tend to migrate during deployment. The migration of a stent during deployment can result in an improper placement of the stent.

To address these difficulties in stent expansion uniformity, the stent 10 described herein is configured with expandable rings 20A at either end of the stent having increased radial strength compared to the expandable middle rings 20. This difference between the configuration of the stent at the middle and ends of the stent results in more even expansion properties of the stent and better crimping properties of the stent.

As shown in FIGS. 1, 1B and 2 the expandable rings 20, 20A are formed by a plurality of struts 22 and a plurality of ductile hinges 24, 24A arranged such that upon expansion, the ductile hinges are deformed while the struts are not deformed or not significantly deformed. The ductile hinge 24, 24A and strut 22 structures are described in further detail in U.S. Pat. No. 6,241,762 which is incorporated herein by reference in its entirety. The ductile hinges 24, 24A can be straight or curved, tapered or of constant width. Preferably, the hinges are somewhat curved and tapered to achieve substantially uniform strain along the length of the hinges. By increasing the widths of the ductile hinges 24, 24A in the end rings 20A compared to the middle rings 20 the stent can be designed for more uniform expansion and improved crimping.

The term "width" as used herein means a dimension of an element in a plane of the cylindrical surface of the stent. The width is generally measured along a line substantially perpendicular to the edges of the element at any particular location along the element. When the edges of the element are not parallel, the width is measured along a line substantially perpendicular to a line bisecting an angle created by the edges of the element.

The rings 20, 20A have alternating open and closed ends. In the arrangement shown in FIG. 2, the closed ends 26 of the rings 20, 20A are aligned with closed ends of adjacent rings and the closed ends are interconnected by the flexible bridging elements 30 or other connecting elements. Structures having aligned adjacent closed ends 26 as shown can be referred to as structures which are substantially 180° out of phase. The expandable rings 20, 20A shown have generally Z-shaped structures. However, the expandable rings may alternatively be formed in any of the other known ring structures including serpentine rings (S-shaped structures), other Z-shaped structures, diamond structures, chevron shapes, or the like which are in phase or out of phase.

The flexible bridging elements 30 are designed with elements having varying widths contoured to distribute strain substantially uniformly along the bridging elements. The contoured shapes of the bridging elements 30 maximizes fatigue strength and flexibility of the bridging elements. Although contoured bridging elements 30 have been shown, many other shaped bridging elements can be used including S-shaped, M-shaped, V-shaped, straight, or other known structures. The bridging elements 30, as shown connect each of the adjacent closed ends 26 forming a closed cell structure. However, every other or every third end can be interconnected forming an open cell structure.

The stent 10 illustrated in FIGS. 1A, 1B, and 2 is also designed with a plurality of holes or reservoir within the struts or other elements which can be non-deforming or substantially non-deforming. The reservoirs allow the stent to deliver one or more beneficial agents which can be delivered luminally, murally, or bi-directionally. The term "beneficial agent" as used herein is intended to have its broadest possible interpretation and is used to include any therapeutic agent or drug, as well as inactive agents such as barrier layers, carrier layers, therapeutic layers, or protective layers. Exemplary classes of therapeutic agents which can be used in the beneficial agent of the present invention include one or more antiproliferatives (paclitaxel and rapamycin), antithrombins (i.e., thrombolytics), immunosuppressants, antilipid agents, anti-inflammatory agents, antineoplastics, antimetabolites, antiplatelets, angiogenic agents, anti-angiogenic agents, vitamins, antimitotics, NO donors, nitric oxide release stimulators, anti-sclerosing agents, vasoactive agents, endothelial growth factors, insulin, insulin growth factors, antioxidants, membrane stabilizing agents, and anti-restenotics. Although beneficial agent reservoirs have been illustrated, the reservoirs can be omitted and the design modified to create a nondrug-eluting stent, a surface coated drug-eluting stent, or a biodegradable stent structure.

As described above, the stent 10 or other expandable medical device includes at least one middle expandable ring 20 formed of a plurality of the substantially rigid struts 22 interconnected by the deformable ductile hinges 24. The ends of the stent 10 are formed by expandable rings 20A located at opposite axial ends of the stent and interconnected to the at least one middle expandable ring 20 by flexible connecting elements 30. The end expandable rings 20A are formed of a plurality of substantially rigid struts 22 interconnected by deformable ductile hinges 24A. To create the uniform expansion and prevent an hourglass shape during expansion, the ductile hinges 24 of the at least one middle expandable ring 20 have a hinge width $W_B$ less than a hinge width $W_A$ of the ductile hinges 24A in the end expandable rings 20A. The stent 10 can open in a uniform manner or with the middle expandable rings 20 opening first to stabilize and prevent migration of the stent during deployment.

In the illustrated embodiment, two ductile hinges 24, 24A are located adjacent each bend in the Z-shaped patterns of the expandable rings 20, 20A. However, the hinges can also be located at other locations, such as, at the apex of an S-shaped pattern. The ductile hinges 24, 24A each have a hinge width $W_A$, $W_B$ which is less than widths of the adjacent struts 22, and the hinges have a hinge length which is less than lengths of the adjacent struts. Thus, the ductile hinges 24, 24A are designed to deform plastically upon radial expansion or compression of the stent 10 while the struts 22 experience no or substantially no plastic deformation upon radial expansion or compression.

In one preferred embodiment, the ductile hinges 24 of the middle expandable rings 20 have a hinge width $W_B$ about 5% to about 50% less than a hinge width $W_A$ of the ductile hinges 20A of the end expandable rings 20A. In another embodiment, the ductile hinges 20 of the middle expandable rings have a hinge width $W_B$ about 5% to about 25% less than a hinge width $W_A$ of the ductile hinges 20A of the end expandable rings 20A.

A strut width of the end expandable rings 20A and the middle expandable rings 20 as shown are substantially the same. However, the strut widths can also be varied, such as, to accommodate differing size reservoirs for delivery of different drugs, or amounts of drugs to the ends and middle of the stent.

In the device illustrated, the ductile hinges 24A of the end expandable rings 20A have a width about 45% to about 55% less than a width of the substantially rigid struts 22 of the end expandable rings. The ductile hinges 24 of the middle expandable rings 20 have a width of about 50% to about 60% less than a width of the substantially rigid struts 22 of the middle expandable rings. These relationships between the strut widths and hinge widths can be varied depending on the particular design of the stent and hinge structure.

In the illustrated embodiment, the end expandable rings 20A having the larger width ductile hinges 24A each have a length which is about 3% to about 30% of an overall length of the expandable medical device. Thus, the strengthen portion of the stent accounts for about 10% to about 60% of the total stent length and is arranged at both ends of the stent. For example, the strengthened portion at one end of the stent can have a length of about 0.5 mm to about 10 mm, preferably about 1 to about 3 mm.

The stent 10 described herein configured with expandable rings 20A at either end of the stent having increased radial strength compared to the expandable middle rings 20 also provides improved crimping and retention characteristics. When a larger width hinge 24A is deformed, as in crimping, an increased force required to deform the hinge results in an increased strain in the hinge for the same deformation. Thus, for the same deformation, the larger hinge 24A has a higher strain and an associated smaller percentage recoil. When the stent is crimped to a uniform diameter, the end rings 20A with the wider hinges 24A will have less recoil than the central rings 20. Thus, the stent 10 is crimped onto a balloon in a shape having narrowed ends. The narrowed ends of the crimped stent 10 help prevent the stent ends from flaring off of the balloon, especially during bending of the stent around corners during advancement. The narrowed ends will also prevent the stent from catching on tissue as the stent is advanced. According to one example, when the stent 10 is crimped onto a balloon, the crimped diameter of the end portions is at least 5% less than the crimped diameter of the middle portion.

In the expanded configuration, the end rings 20A having the wider hinges 24A have greater strength than the middle rings 30. This greater strength at the stent ends minimize the tendency of the stent to taper inward at the ends after deployment which can be caused by the natural inward constriction force of the vessel.

While the invention has been described in detail with reference to the preferred embodiments thereof, it will be apparent to one skilled in the art that various changes and modifications can be made and equivalents employed, without departing from the present invention.

What is claimed is:

1. A stent comprising:
    a plurality of struts and a plurality of ductile hinges, wherein the ductile hinges are capable of deforming plastically upon radial expansion or compression of the stent while the struts are designed to experience substantially no plastic deformation upon radial expansion or compression;
    a portion of the plurality of ductile hinges located at axial ends of the stent with a larger width than a remainder of the plurality of ductile hinges, wherein each of the axial ends of the stent with the larger width ductile hinges extend for about 3% to about 30% of the length of the stent.

2. The stent of claim 1, further comprising wherein the crimped center portion of the stent with at least one middle expandable ring formed of a plurality of substantially rigid struts interconnected by deformable ductile hinges and the opposite end portions of the stent comprise two end expandable rings, located one at each opposite axial end of the stent, the end expandable rings formed of a plurality of substantially rigid struts interconnected by deformable ductile hinges, and wherein the ductile hinges of the at least one middle expandable ring have a hinge width less than a hinge width of the ductile hinges of the end expandable rings.

3. The device of claim 2, wherein at least two end expandable rings and the at least one middle expandable ring are formed in S-shaped or Z-shaped patterns.

4. The device of claim 3, wherein two ductile hinges are located adjacent each bend in the S-shaped or Z-shaped patterns.

5. The device of claim 2, wherein the ductile hinges each have a hinge width which is less than adjacent struts, and the hinges have a hinge length which is less than adjacent struts.

6. The device of claim 2, wherein the ductile hinges are designed to deform plastically upon radial expansion or compression of the expandable medical device while the struts experience no plastic deformation upon radial expansion or compression.

7. The device of claim 2, wherein the ductile hinges of the at least one middle expandable ring have a hinge width about 5% to about 50% less than a hinge width of the ductile hinges of the end expandable rings.

8. The device of claim 1, wherein the center portion of the stent has ductile hinges with a hinge width about 50% to about 25% less than a hinge width of ductile hinges of the opposite end portions.

9. The device of claim 2, wherein the substantially rigid struts of the end expandable rings and the middle expandable rings have a strut width which is substantially the same.

10. The device of claim 2, wherein the end expandable rings having the larger width ductile hinges each have a length which is about 3% to about 30% of an overall length of the stent.

11. A method of improving crimping of stents onto balloons, the method comprising:
    forming a stent with a plurality of struts and a plurality of ductile hinges, wherein the ductile hinges are designed to deform plastically upon radial expansion or compression of the stent while the struts experience substantially no plastic deformation upon radial expansion or compression;
    forming a portion of the plurality of ductile hinges located at axial ends of the stent with a larger width than a remainder of the plurality of ductile hinges, wherein each of the axial ends of the stent with the larger width ductile hinges extend for about 3% to about 30% of the length of the stent;
    crimping the stent onto a balloon catheter by compressing the stent to a uniform crimped diameter along the axis of the stent; and
    releasing the compressive force of crimping and causing the stent to recoil a first percentage at the axial ends of the stent and a second percentage at a middle portion of the stent, wherein the second percentage is greater than the first percentage.

12. A method of improving crimping of stents onto balloons, the method comprising:

forming a stent with a plurality of struts and a plurality of ductile hinges, wherein the ductile hinges are designed to deform plastically upon radial expansion or compression of the stent while the struts experience substantially no plastic deformation upon radial expansion or compression;

forming a portion of the plurality of ductile hinges located at axial ends of the stent with a larger width than a remainder of the plurality of ductile hinges;

crimping the stent onto a balloon catheter by compressing the stent to a uniform crimped diameter along the axis of the stent; and releasing the compressive force of crimping and causing the stent to recoil a first percentage at the axial ends of the stent and a second percentage at a middle portion of the stent, wherein the second percentage is greater than the first percentage;

wherein a crimped diameter of the axial ends is at least 5% less than a crimped diameter of the middle portion of the stent.

* * * * *